United States Patent
Tomono et al.

(10) Patent No.: US 11,543,392 B2
(45) Date of Patent: Jan. 3, 2023

(54) LIQUID CHROMATOGRAPH AND DISSOLUTION TEST SYSTEM

(71) Applicant: SHIMADZU CORPORATION, Kyoto (JP)

(72) Inventors: Taichi Tomono, Kyoto (JP); Takayuki Iriki, Kyoto (JP); Tomohiro Shagawa, Kyoto (JP); Satoru Watanabe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/535,774

(22) Filed: Nov. 26, 2021

(65) Prior Publication Data

US 2022/0082533 A1    Mar. 17, 2022

Related U.S. Application Data

(62) Division of application No. 16/631,508, filed as application No. PCT/JP2017/030628 on Aug. 25, 2017, now Pat. No. 11,243,191.

(51) Int. Cl.
*G01N 30/24* (2006.01)
*G01N 35/10* (2006.01)
(Continued)

(52) U.S. Cl.
CPC .............. *G01N 30/24* (2013.01); *G01N 13/00* (2013.01); *G01N 35/0092* (2013.01);
(Continued)

(58) Field of Classification Search
CPC .............. G01N 13/00; G01N 2013/006; G01N 2035/00198
See application file for complete search history.

(56) References Cited

U.S. PATENT DOCUMENTS 4,678,639 A * 7/1987 Dong ............. G01N 13/00
436/52
6,060,024 A * 5/2000 Hutchins ........... G01N 13/00
73/866
(Continued)

FOREIGN PATENT DOCUMENTS

| JP | 2006-118985 A | 5/2006 |
| JP | 2016-502101 A | 1/2016 |
| JP | 2016-206162 A | 12/2016 |

OTHER PUBLICATIONS

International Search Report for corresponding Application No. PCT/JP2017/030628, dated Nov. 7, 2017.
(Continued)

*Primary Examiner* — Justin N Olamit
(74) *Attorney, Agent, or Firm* — Renner, Otto, Boisselle & Sklar, LLP

(57) ABSTRACT

An online HPLC dissolution test system includes a dissolution tester and a liquid chromatograph. An autosampler of the liquid chromatograph includes at least one flow vial, a sampling needle and an injection port. the flow vial is connected to the dissolution tester via a pipe and is for storing a sample solution supplied from the dissolution tester therein. The sampling needle is for collecting the sample solution by sucking from the flow vial. The injection port is for injecting the sample solution from the sampling needle into the analysis channel. The controller of the liquid chromatograph includes an immediate analyzing execution part configured to cause the autosampler to execute immediate analyzing operation for sucking the sample solution in the flow vial with the sampling needle and directly injecting the sample solution into the injection port when the sample solution is supplied from the dissolution tester to the flow vial.

2 Claims, 6 Drawing Sheets

(51) Int. Cl.
    *G01N 35/00*         (2006.01)
    *G01N 13/00*         (2006.01)
    *G01N 30/02*         (2006.01)

(52) U.S. Cl.
    CPC ... *G01N 35/1009* (2013.01); *G01N 2013/006* (2013.01); *G01N 2030/027* (2013.01); *G01N 2035/00198* (2013.01)

(56) References Cited

U.S. PATENT DOCUMENTS

| | | | |
|---|---|---|---|
| 10,732,080 B1 * | 8/2020 | Whitkanack | G01N 1/4055 |
| 2014/0174207 A1 | 6/2014 | Clay | |

OTHER PUBLICATIONS

Written Opinion for corresponding Application No. PCT/JP2017/030628, dated Nov. 7, 2017.

\* cited by examiner

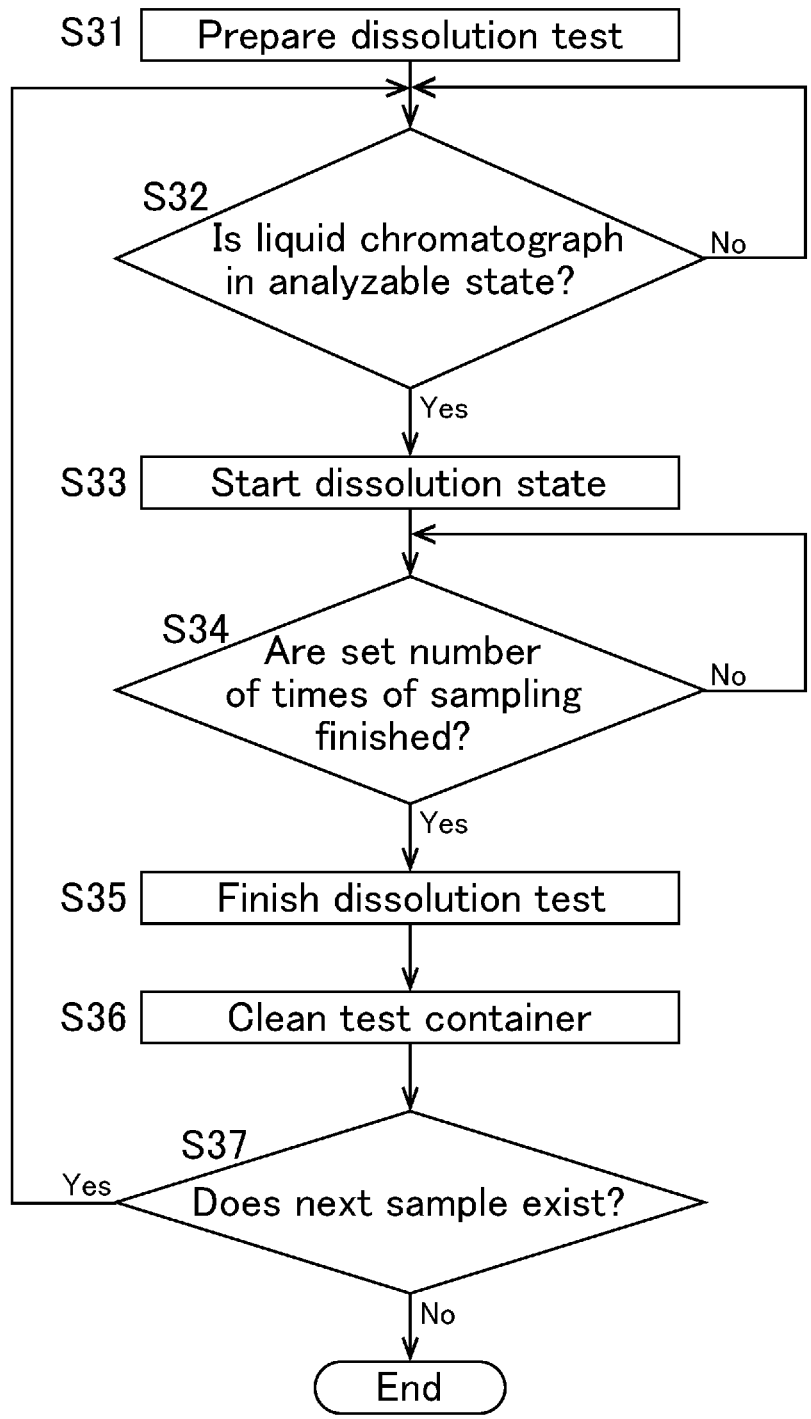

LIQUID CHROMATOGRAPH AND DISSOLUTION TEST SYSTEM

This is a divisional under 35 USC § 121 of U.S. application Ser. No. 16/631,508, filed Jan. 16, 2020, which is a national stage under USC § 371 of International Application No. PCT/JP2017/030628, filed Aug. 25, 2017, the entire disclosures of which are incorporated herein by reference in their entirety.

TECHNICAL FIELD

The present invention relates to a liquid chromatograph for online analysis of a test solution of a dissolution tester and a dissolution test system (hereinafter referred to as an online HPLC dissolution test system) equipped with the liquid chromatograph.

BACKGROUND ART

An automatic dissolution tester equipped with a fraction function and an online measurement function using a UV spectrometer is expected to have a large market scale also in the future. A dissolution tester is generally connected to a UV spectrometer, and the concentration of a specific component in a sample solution from the dissolution tester is measured using a UV spectrometer at each preset timing, so that a dissolution rate of a sample, such as an internal solid preparation, into liquid is measured.

On the other hand, in the dissolution test of an internal solid preparation, a liquid chromatograph is sometimes used in a case where an accurate dissolution test is difficult with a UV spectrometer due to the presence of a plurality of components or the influence of an excipient (see Patent Document 1). In that case, a flow vial is sometimes installed in an autosampler of the liquid chromatograph so that the sample solution of the dissolution tester can be introduced into the liquid chromatograph online. Such a dissolution test system is referred to as an online high performance liquid chromatograph dissolution test system.

PRIOR ART DOCUMENT

Patent Document

Patent Document 1: Japanese Patent Laid-open Publication No. 2006-118985

SUMMARY OF THE INVENTION

Problems to be Solved by the Invention

Since a conventional liquid chromatograph has required a long time for one analysis, there has been a situation that the analysis speed of the liquid chromatograph cannot catch up with the sampling speed of a sample solution from a dissolution tester. For this reason, a conventional online HPLC dissolution test system has had a configuration, in which a sample solution supplied from a dissolution tester is temporarily collected in an empty collection container and, when a liquid chromatograph becomes ready for analysis, the sample solution is collected from the collection container and injected into an analysis channel to start analysis. For this reason, there has been a problem of poor efficiency in a dissolution test.

Further, in recent years, analysis of a liquid chromatograph has been accelerated, and the time required for one analysis has been rapidly shortened compared to the conventional case. Furthermore, a fully automatic dissolution tester capable of continuous dissolution testing of a plurality of types of internal solid preparations has been developed. From such a background, it is considered possible to perform a dissolution test with higher efficiency if a fully automatic dissolution tester is successfully combined with a liquid chromatograph whose analysis has been accelerated.

In view of the above, an object of the present invention is to enable a dissolution test to be performed with higher efficiency than before by using a liquid chromatograph.

Solutions to the Problems

A liquid chromatograph according to the present invention includes an analysis channel through which a mobile phase flows, an autosampler configured to inject a sample solution supplied from a dissolution tester into the analysis channel, an analysis column separating individual components in the sample solution injected into the analysis channel by the autosampler, a detector detecting the components separated by the analysis column, and a controller configured to control operation of at least the autosampler.

Then, the autosampler comprises at least one flow vial, a sampling needle and an injection port, the flow vial is connected to the dissolution tester via a pipe and is for storing a sample solution supplied from the dissolution tester therein, the sampling needle is for collecting the sample solution by sucking from the flow vial, and the injection port is for injecting the sample solution from the sampling needle into the analysis channel. Furthermore, the controller includes an immediate analyzing execution part configured to cause the autosampler to execute immediate analyzing operation for sucking the sample solution in the flow vial with the sampling needle and directly injecting the sample solution into the injection port when the sample solution is supplied from the dissolution tester to the flow vial.

That is, in addition to or in place of a conventional analysis system, in which a sample solution is supplied from the dissolution tester is temporarily collected in a collection container, and the sample is sucked from the collection container and injected into an analysis channel when analysis by the liquid chromatograph is possible, the liquid chromatograph according to the present invention employs an immediate analysis system, in which a sample solution supplied from the dissolution tester is sucked with the sampling needle and directly injected into the injection port without using the collection container. This is realized by increasing the analysis speed of the liquid chromatograph, and assumes that the liquid chromatograph is analyzed at a speed higher than the sampling speed of the dissolution tester. Since the sample solution supplied from the dissolution tester is directly injected into the injection port without using the collection container, the operation in which the sampling needle discharges the sample solution into the collection container or the operation in which the sample solution is sucked from the collection container again and injected into the injection port is omitted, and the dissolution test can be performed with high efficiency. Then, since the sample solution sampled from the dissolution tester can be immediately analyzed with the liquid chromatograph, a result of the dissolution test can be quickly acquired.

In the liquid chromatograph of the present invention, the dissolution test of a conventional system, in which the sample solution supplied from the dissolution tester is temporarily collected in a collection container, and the sample is sucked from the collection container and injected into the analysis channel when analysis by the liquid chromatograph is possible, can be preferably performed. The dissolution test of the conventional system, in which a sample solution is temporarily collected in the collection container, has an advantage that the sample solution can be stored in the collection container. This system is effective in a case where a change in the dissolution rate of a sample over time needs to be observed (in a cycle shorter than the analysis time of the liquid chromatograph), or in a case where a compound that requires a long analysis time or a compound that requires dilution is the sample. Therefore, if the dissolution test of the conventional system can also be performed, the dissolution test can be performed under an appropriate condition according to a sample.

A specific configuration of the above aspect, the autosampler includes at least one collection container for collecting a sample solution collected from the flow vial by the sampling needle while fractionating the sample solution from other sample solutions. The controller further includes a collecting operation execution part and a collected sample analyzing execution part. The collecting operation execution part is configured to cause the autosampler to execute collecting operation for sucking a sample solution in the flow vial with the sampling needle and discharging the sample solution from the sampling needle into the collection container when the sample solution is supplied from the dissolution tester to the flow vial. The collected sample analyzing execution part is configured to cause the autosampler to execute collected sample analyzing operation for sucking the sample solution collected in the collection container with the sampling needle and injecting the sample solution into the injection port.

Furthermore, the liquid chromatograph of the present invention preferably further includes a mode selector configured to select either the immediate analyzing mode or the collection analyzing mode based on an instruction inputted by the operator. In such a case, the immediate analyzing execution part is configured to cause the autosampler to execute the immediate analyzing operation when the immediate analyzing mode is selected by the mode selector, and the collecting operation execution part and the collected sample analyzing execution part are configured to cause the autosampler to execute the collecting operation and the collected sample analyzing operation, respectively, when the collection analyzing mode is selected by the mode selector. In this manner, the operator can freely select the immediate analyzing mode and the collection analyzing mode, and the degree of freedom in setting a condition for the dissolution test is increased.

A dissolution test system according to the present invention includes a dissolution tester, and the liquid chromatograph described above connected to the dissolution tester via a pipe.

Further, as described above, although a fully automatic dissolution tester that can automatically and continuously perform dissolution tests on a plurality of types of internal solid preparations has been developed, such a fully automatic dissolution tester is generally combined with a UV spectrometer, and has not been able to perform fully automatic continuous dissolution tests in combination with a liquid chromatograph. For this reason, in a case where a plurality of solid preparations that have a plurality of components exist, the operator has needed to monitor the analysis state in the liquid chromatograph, and start the dissolution test for a next new sample when the liquid chromatograph becomes in an analyzable state.

In view of the above, the dissolution test system according to the present invention is preferably configured to be able to execute the dissolution test for a plurality of solid preparations that have a plurality of components, even in a case where such solid preparations exist, by linking the dissolution tester and a liquid chromatograph.

That is, the dissolution test system according to the present invention preferably has a configuration, in which the liquid chromatograph includes an analysis state communicating part which is configured to determine whether or not the liquid chromatograph is in analyzing operation and to transmit an analysis state signal regarding whether or not the liquid chromatograph is in analyzing operation to the dissolution tester, and the dissolution tester includes a communicating part for receiving the analysis state signal transmitted by the analysis state communicating part, and is configured not to start a dissolution test for a new sample when the liquid chromatograph is in analyzing operation and start a dissolution test for the new sample when analyzing operation of the liquid chromatograph is finished, based on the analysis state signal received by the communicating part in a case where a dissolution test is set to be executed continuously for a plurality of samples. In the above manner, when the liquid chromatograph becomes in an analyzable state, the dissolution tester automatically starts the dissolution test for a next sample. Accordingly, the operator no longer needs to monitor the analysis state of the liquid chromatograph, and the dissolution test of a plurality of samples can be executed continuously in a fully automatic manner.

Further, the liquid chromatograph used in the dissolution test system described above preferably includes an analysis channel through which a mobile phase flows, an autosampler configured to inject a sample solution supplied from the dissolution tester into the analysis channel, an analysis column for separating individual components in the sample solution injected into the analysis channel by the autosampler, a detector for detecting the components separated by the analysis column, a controller configured to control operation of at least the autosampler, and an analysis state communicating part configured to determine whether or not the liquid chromatograph is in analyzing operation and transmit an analysis state signal regarding whether or not the liquid chromatograph is in analyzing operation to the dissolution tester, and, when the dissolution tester starts a dissolution test for the new sample, analyzing operation for the new sample is performed.

Further, the dissolution tester used in the dissolution test system described above preferably has a configuration, in which the dissolution tester includes a communicating part configured to receive the analysis state signal transmitted by the analysis state communicating part, and is configured not to start a dissolution test for a new sample when the liquid chromatograph is in analyzing operation and start a dissolution test for the new sample when analyzing operation of the liquid chromatograph is finished, based on the analysis state signal received by the communicating part in a case where a dissolution test is set to be executed continuously for a plurality of samples.

Effects of the Invention

In a liquid chromatograph and a dissolution test system according to the present invention, a sample solution supplied from a dissolution tester is directly injected into an injection port, so that a dissolution test can be performed with high efficiency. Then, since the sample solution sampled from the dissolution tester can be immediately analyzed with the liquid chromatograph, a result of the dissolution test can be quickly acquired.

BRIEF DESCRIPTION OF THE DRAWINGS

FIG. 6 is a flowchart for explaining an example of operation of a fully automatic continuous dissolution test according to the embodiment.

EMBODIMENT OF THE INVENTION

Figure 1:
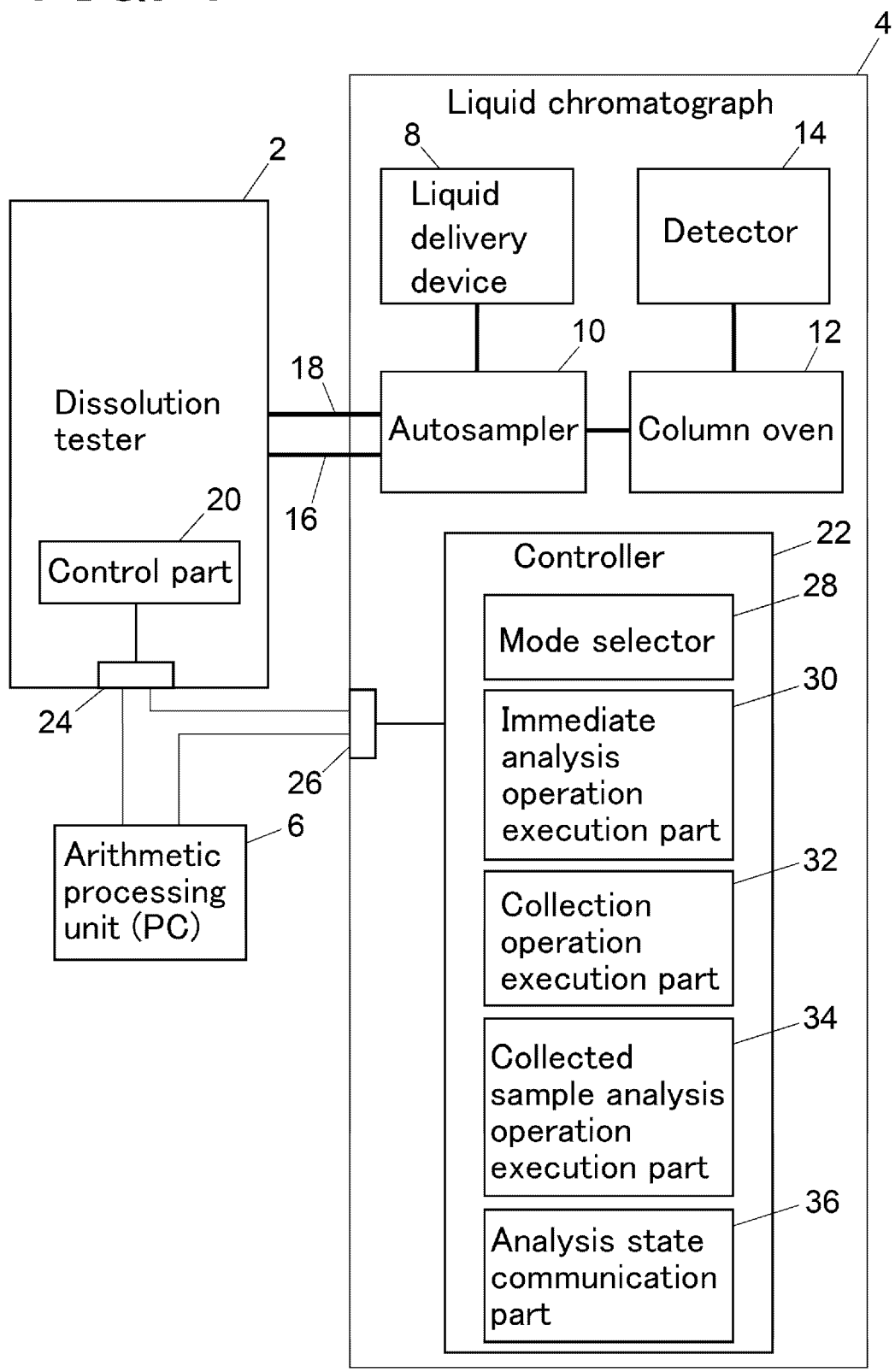
FIG. 1 is a schematic configuration diagram showing an embodiment of an online HPLC dissolution test system.

Hereinafter, an embodiment of a liquid chromatograph, a dissolution tester, and a dissolution test system according to the present invention will be described with reference to the drawings.

An online HPLC dissolution test system of the present embodiment includes a dissolution tester 2, a liquid chromatograph 4, and an arithmetic processing part 6. Although not shown in the drawings, the dissolution tester 2 has at least one test container for storing a sample, such as a medicine, together with liquid, and is configured to supply the solution in the test container as a sample solution to an autosampler 10 of the liquid chromatograph 4 via an inlet pipe 16 at every preset time. The arithmetic processing part 6 is electrically connected to a controller 20 of the dissolution tester 2 via a communication interface 24 (communicating part) and to a controller 22 of the liquid chromatograph 4 via a communication interface 26.

The arithmetic processing part 6 is realized by a dedicated computer or a general-purpose personal computer. An operator can centrally manage the entire online HPLC dissolution test system via the arithmetic processing part 6. The controller 20 of the dissolution tester 2 is realized by a microcomputer or the like provided for controlling operation of each element provided in the dissolution tester. The controller 22 of the liquid chromatograph 4 is realized by, for example, a system controller that manages operation of modules 8, 10, 12, and 14 of the liquid chromatograph 4.

The liquid chromatograph 4 includes a liquid delivery device 8, the autosampler 10, a column oven 12, a detector 14, and the controller 22.

The liquid delivery device 8 is a device for delivering a mobile phase using a liquid delivery pump. An outlet of the liquid delivery device 8 is connected to the autosampler 10 via a pipe.

The autosampler 10 is configured to inject a sample solution supplied from the dissolution tester 2 into the analysis channel through which a mobile phase from the liquid delivery device 8 flows. A configuration of the autosampler 10 will be described later.

In the column oven 12, an analysis column (not shown) for separating a sample into individual components is stored. The analysis column in the column oven 12 is connected to an outlet of the autosampler 10 with a pipe interposed between them and has a configuration in which a sample injected by the autosampler 10 is introduced into the analysis column together with the mobile phase from the liquid delivery device 8. A downstream end of the analysis column in the column oven 12 is connected to a detector 14 with a pipe interposed between them.

The detector 14 is for detecting components separated by the analysis column, and is, for example, an ultraviolet absorbance detector. A detector signal obtained by the detector 14 is taken into the arithmetic processing part 6 and used for quantification of a component concentration, and the like.

Figure 2:
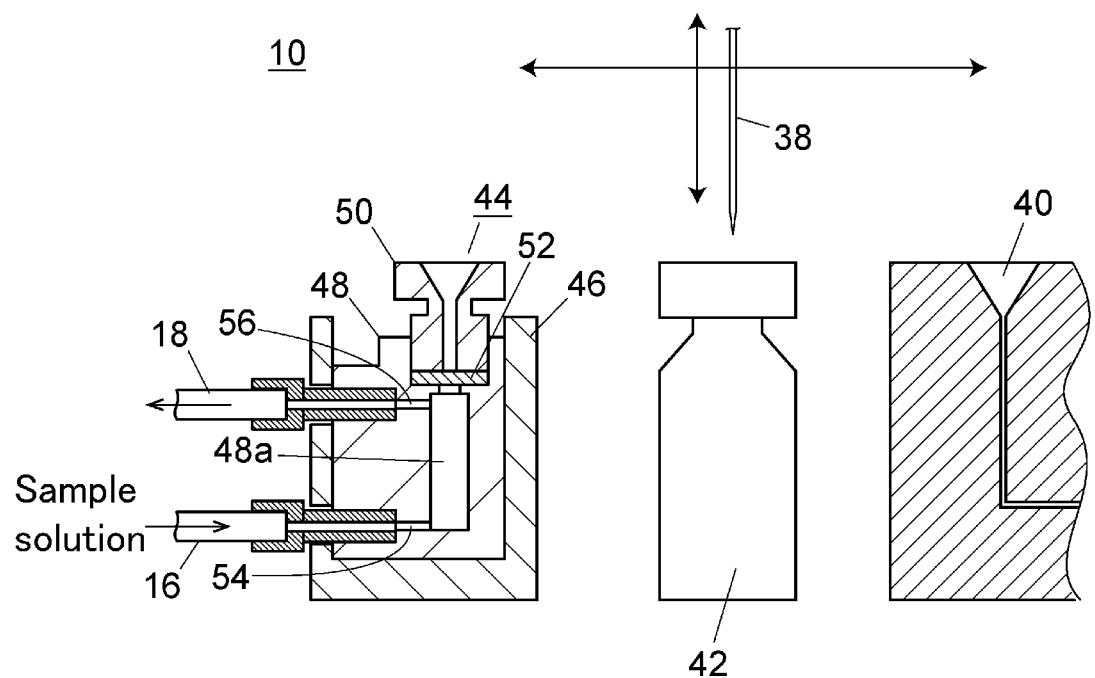
FIG. 2 is a schematic partial cross-sectional configuration diagram showing an example of a configuration in an autosampler of the embodiment.

Here, a schematic configuration of the autosampler 10 will be described with reference to FIG. 2.

In the autosampler 10, a sampling needle 38, an injection port 40, a collection container 42, and a flow vial 44 are provided. In the diagram, for the sake of convenience, only one of each of the collection container 42 and the flow vial 44 is shown, however, a plurality of the collection containers 42 and the flow vials 44 are actually provided. The number of the collection containers 42 and the flow vials 44 is not limited. The flow vial 44 is held in a flow vial rack 46.

The injection port 40 is for the sampling needle 38 to inject a sample solution into the analysis channel through which a mobile phase flows. The injection port 40 is configured to allow the tip of the sampling needle 38 to be inserted and the sampling needle 38 to be connected in a liquid-tight manner.

The collection container 42 is a container for fractionating and collecting a sample solution that the sampling needle 38 collects from the flow vial 44.

The flow vial 44 includes a flow vial main body 48 and a cap 50 attached to an upper part of the flow vial main body 48. Inside the flow vial main body 48, space 48a for storing a sample solution, an inlet portion 54 that is a channel leading to a bottom of the space 48a, and an outlet portion 56 that is a channel leading to an upper part of the space 48a are provided. The inlet pipe 16 is connected to the inlet portion 54, and an outlet pipe 18 is connected to the outlet portion 56. An upper portion of the flow vial main body 48 is opened, and the opening is sealed by a septum 52 made from an elastic material. The cap 50 is attached to the upper part of the flow vial main body 48 so as to press down the septum 52. An opening leading to the septum 52 is provided on an upper surface of the cap 50. The opening of the cap 52 is for guiding the sampling needle 38 descending from above to the space 48a in the flow vial main body 48. The sampling needle 38 that descends through the opening of the cap 50 penetrates the septum 52 and allows the tip to advance into the space 48a in the flow vial main body 48 to suck the sample solution.

The sampling needle 38 is provided above the injection port 40, the collection container 42, and the flow vial rack 46. The sampling needle 38 is moved in a horizontal plane direction and a vertical direction by a moving mechanism (not shown) in a state where the tip is directed vertically downward.

As operation modes of the liquid chromatograph 4, there are two types of modes, an immediate analyzing mode and a collection analyzing mode. In the immediate analyzing mode, the sampling needle 38 of the autosampler 10 performs immediate analyzing operation in which a sample is sucked from the flow vial 44 and directly injected into the injection port 40. On the other hand, in the collection analyzing mode, the sampling needle 38 performs collecting operation, in which a sample solution is sucked from the flow vial 44 and the sample solution is collected in the collection container 42, and collected sample analyzing operation, in which the sample solution is sucked from the collection container 42 and injected into the injection port 40.

The sample solution injected through the injection port 40 is then introduced into the detector 14 via the analysis column in the column oven 12 by a mobile phase from the liquid delivery device 8. Note that, although not shown in FIG. 2, the autosampler 10 is also provided with a standard sample container that stores a standard sample for quantifying the concentration of a specific component in sample water, and the sampling needle 38 can suck the standard sample from the standard sample container and injects the standard sample into the injection port 40.

Returning to FIG. 1, description of one embodiment of the online HPLC dissolution test system will be continued. The controller 22 of the liquid chromatograph 4 includes a mode selector 28, an immediate analyzing execution part 30, a collecting operation execution part 32, a collected sample analyzing execution part 34, and an analysis state communicating part 36. Each of these parts 28, 30, 32, 34, and 36 is a function obtained when an arithmetic element, such as a microcomputer, provided in the controller 22 executes a predetermined program.

The mode selector 28 is configured to select one of the immediate analyzing mode and the collection analyzing mode as an operation mode of the liquid chromatograph 4 based on an input instruction from the operator. That is, the operator can designate one of the immediate analyzing mode and the collection analyzing mode as the operation mode of the liquid chromatograph 4 in a dissolution test for a certain sample.

As described above, the immediate analyzing mode is a mode, in which, when the sample solution is supplied from the dissolution tester 2 to the flow vial 44 of the autosampler 10, the autosampler is caused to execute the immediate analyzing operation of sucking the sample solution with the sampling needle 38 and injecting the sample solution directly into the injection port 40. That is, the immediate analyzing mode is a mode in which the analysis by the liquid chromatograph is started immediately when the sample solution is supplied from the dissolution tester 2 to the flow vial 44 of the autosampler 10. On the other hand, the collection analyzing mode is a mode, in which, when the sample solution is supplied from the dissolution tester 2 to the flow vial 44 of the autosampler 10, the autosampler is caused to execute the collecting operation of sucking the sample solution with the sampling needle 38 and collecting the sample solution in the empty collection container 42, and the collected sample analyzing operation of collecting the sample solution from the collection container 42 at a predetermined timing and injecting the sample solution into the injection port 40.

The operation mode of the liquid chromatograph 4 can be set for each sample. That is, in a case where there exists a plurality of samples, for which the dissolution test is to be performed, the operation mode of the liquid chromatograph 4 in the dissolution test for each sample can be set.

The immediate analyzing execution part 30 is configured to cause the autosampler 10 to execute the above-described measurement analyzing operation when the immediate analyzing mode is selected by the mode selector 28.

The collecting operation execution part 32 and the collected sample analyzing execution part 34 are configured to cause the autosampler 10 to execute the above-described collecting operation and collected sample analyzing operation when the collection analyzing mode is selected by the mode selector 28.

The analysis state communicating part 36 is configured to determine whether or not the liquid chromatograph 4 is under analysis, and transmit an analysis state signal related to the determination result to the dissolution tester 2 directly, or indirectly via the arithmetic processing part 6. Whether or not the liquid chromatograph 4 is under analysis can be determined depends on whether or not a preset analysis time has elapsed, whether or not a last peak of a chromatogram obtained by a detection signal of the detector 14 has appeared, and the like.

Figure 3:
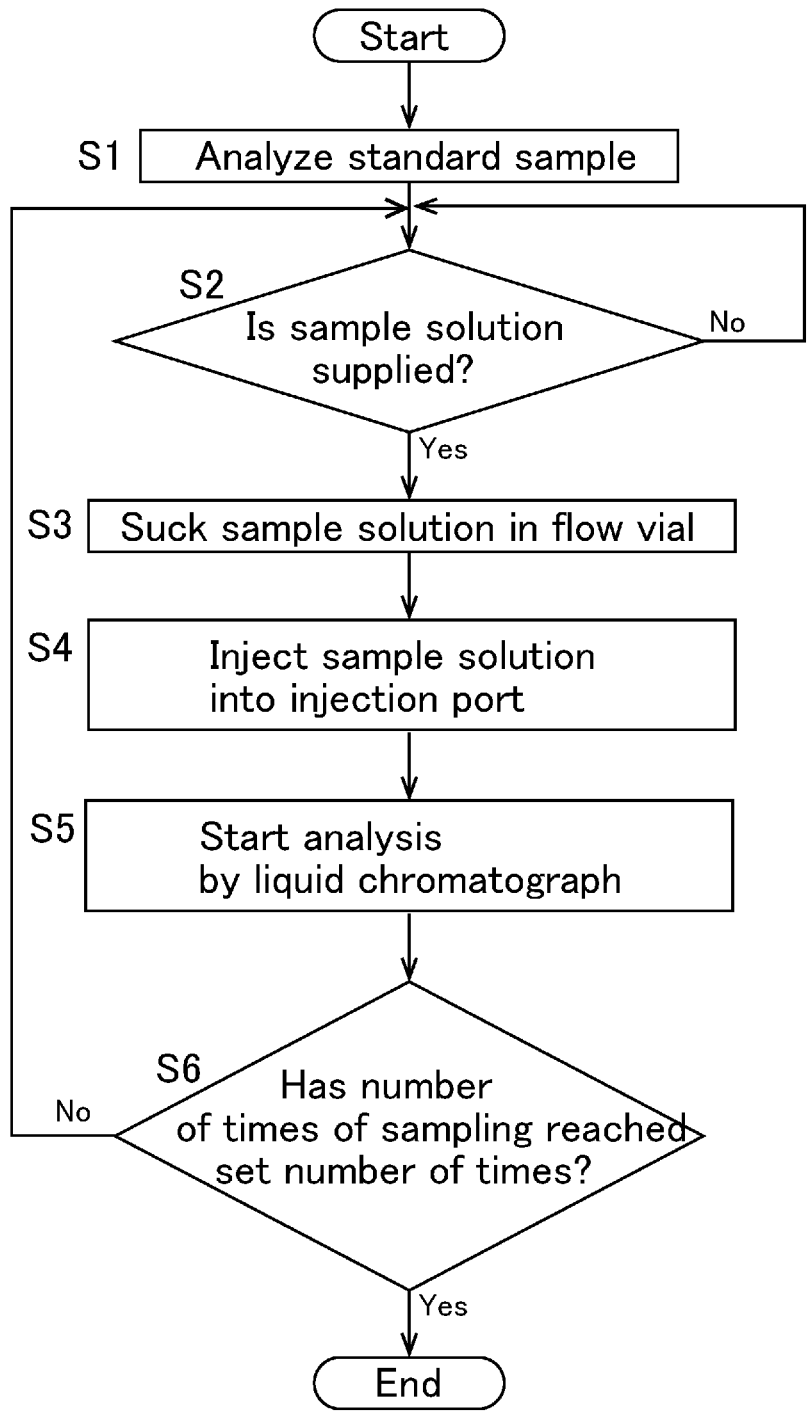
FIG. 3 is a flowchart for explaining an example of immediate analyzing operation of the embodiment.

Next, the immediate analyzing operation of the liquid chromatograph 4 in the immediate analyzing mode will be described using a flowchart of FIG. 3 together with FIGS. 1 and 2.

First, before the dissolution test of a sample is started, a standard sample whose specific component concentration is known is analyzed, and the measurement data is recorded (Step S1). After the analysis of the standard sample is finished, the dissolution test of the sample by the dissolution tester 2 is started. From the dissolution tester 2, the sample solution is supplied to the flow vial 44 of the autosampler 10 at a preset timing (for example, at regular intervals) (Step S2). When the sample solution is supplied to the flow vial 44, a signal indicating that the sample solution is supplied is transmitted from the controller 20 of the dissolution tester 2 to the controller 22 of the liquid chromatograph 4.

When the sample solution is supplied from the dissolution tester 2 to the flow vial 44, the immediate analyzing execution part 30 causes the autosampler 10 to execute operation of sucking the sample solution in the flow vial 44 with the sampling needle 38 and directly injecting the sample solution into the injection port 40 (Steps S3 and S4). The sample injected into the injection port 40 is introduced into the analysis channel, through which the mobile phase from the liquid delivery device 8 flows, and analysis by the liquid chromatograph is performed (Step S5).

The operations in Steps S1 to S5 described above are repeatedly executed as many times as preset by the operator (Step S6).

Figure 4:
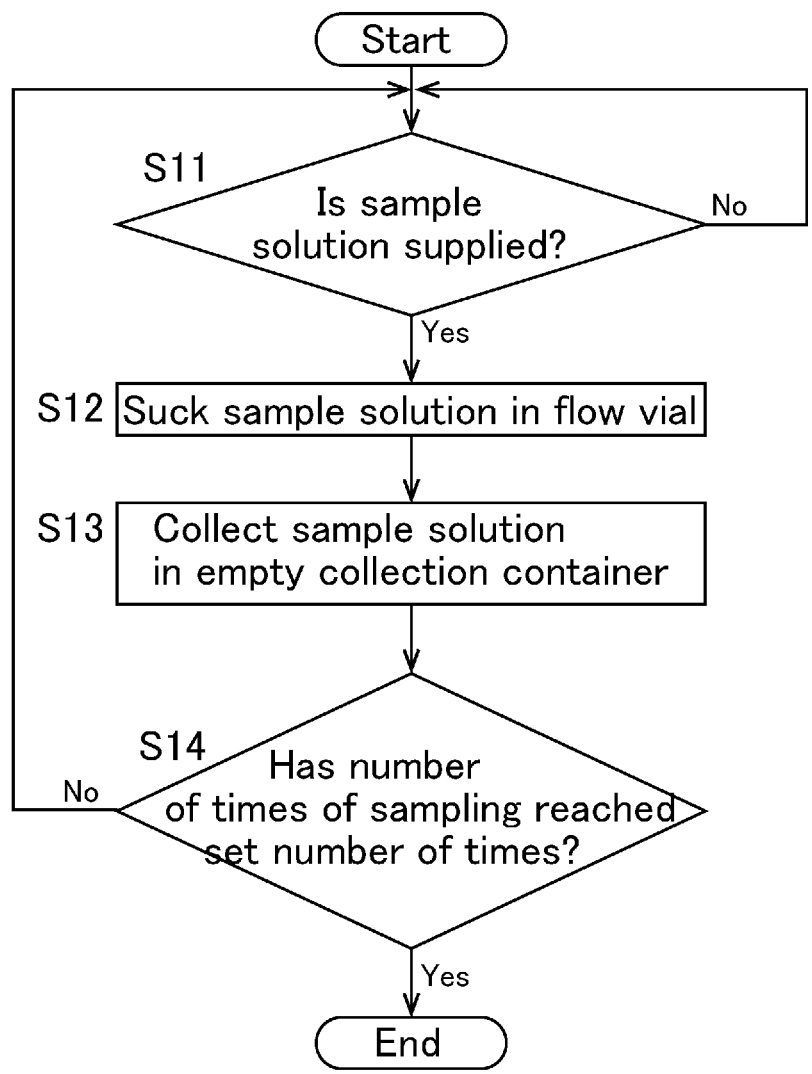
FIG. 4 is a flowchart for explaining an example of collecting operation of the embodiment.

Next, the collecting operation of the liquid chromatograph 4 in the collection analyzing mode will be described using a flowchart of FIG. 4 together with FIGS. 1 and 2.

The dissolution test of a sample in the dissolution tester 2 is started. From the dissolution tester 2, the sample solution is supplied to the flow vial 44 of the autosampler 10 at a preset timing (Step S11).

When the sample solution is supplied from the dissolution tester 2 to the flow vial 44, the collecting operation execution part 32 causes the autosampler 10 to execute operation of sucking the sample solution in the flow vial 44 with the sampling needle 38 and discharging the sample solution to the empty collection container 42 to collect the sample solution (Steps S12 and S13). The above operations in Steps S11 to S13 are repeatedly executed as many times as preset by the operator (Step S14).

Figure 5:
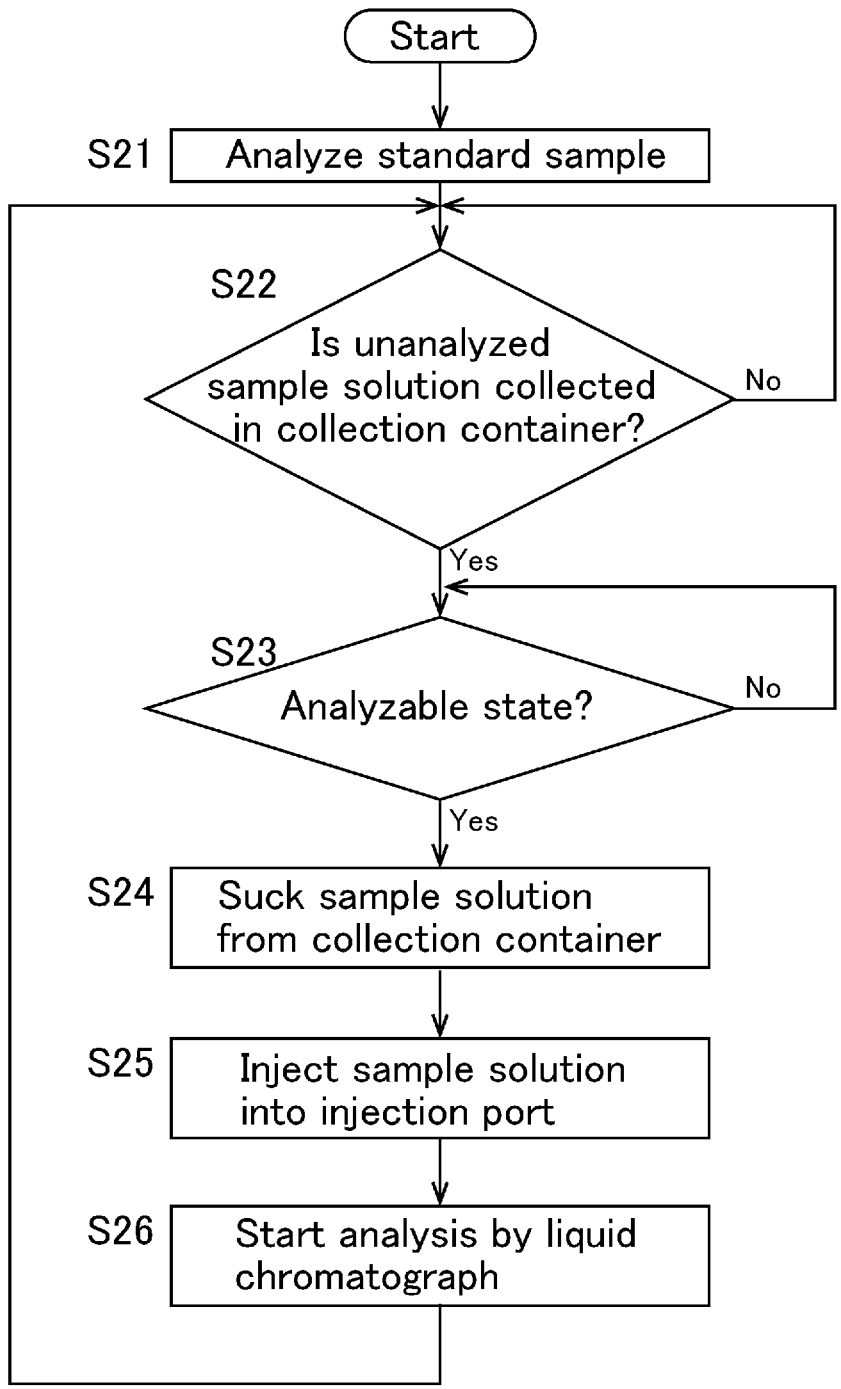
FIG. 5 is a flowchart for explaining an example of collected sample analyzing operation of the embodiment.

Next, the collected sample analyzing operation of the liquid chromatograph 4 in the collection analyzing mode will be described using a flowchart of FIG. 5 together with FIGS. 1 and 2.

This collected sample analyzing operation can be executed at an optional timing as long as it is after an unanalyzed sample solution is collected in at least one collection container. The operator can optionally set the timing of executing the collected sample analyzing operation.

Like the immediate analyzing mode, before the dissolution test of a sample is started, a standard sample whose specific component concentration is known is analyzed, and the measurement data is recorded (Step S21). After the above, when an unanalyzed sample solution is collected in the collection container 42 (Step S22), the collected sample analyzing execution part 34 determines whether the liquid chromatograph 4 is in an analyzable state, that is, whether the liquid chromatograph 4 is not in the middle of analysis (Step S23). In a case where the liquid chromatograph 4 is in an analyzable state, the collected sample analyzing execution part 34 causes the autosampler 10 to execute operation of sucking the sample solution from the collection container 42 with the sampling needle 38 and injecting the sample solution into the injection port 40 (Steps S24 and S25). The sample injected into the injection port 40 is introduced into the analysis channel through which the mobile phase from the liquid delivery device 8 flows, and is analyzed with the liquid chromatograph (Step S26). The operations in Steps S22 to S26 described above are repeated for the number of collection containers in which an unanalyzed sample solution is collected.

Further, the online HPLC dissolution test system of the present embodiment has a configuration, in which the dissolution tester 2 and the liquid chromatograph 4 are linked by communication, so that a fully automatic continuous dissolution test is executed for a plurality of samples. As a premise of the above, the dissolution tester 2 can be installed with a plurality of samples. The dissolution tester 2 is configured in such a way that, in a case where a plurality of types of samples are set, each of the samples is sequentially introduced into a test container, and the dissolution test for the sample is automatically executed.

An example of the operation of the fully automatic continuous dissolution test will be described using the flowchart of FIG. 6 together with FIG. 1.

First, the operator prepares for the fully automatic continuous dissolution test (Step S31). The preparation includes installation of the sample in the dissolution tester 2, the setting of a condition for the dissolution test for each sample, and the like. When the operator inputs an instruction to start the dissolution test via the arithmetic processing part 6 after the preparation is completed, the controller 20 of the dissolution tester 2 determines whether or not the liquid chromatograph 4 is in an analyzable state based on an analysis state signal transmitted from the analysis state communicating part 36 of the liquid chromatograph 4 (Step S32). If the liquid chromatograph 4 is in an analyzable state, the dissolution test for the sample is started (Step S33).

After the dissolution test is started, the sample solution is supplied from the dissolution tester 2 to the autosampler 10 of the liquid chromatograph 4 at the timing set by the operator, and sampling of the sample solution is performed in the autosampler 10 (Step S34). The analyzing operation by the liquid chromatograph 4 is as described above with reference to FIGS. 3 to 5. When the number of times of sampling of the sample solution reaches a preset number, the dissolution tester 2 finishes the dissolution test (Step S35) and cleans the test container (Step S36). The liquid chromatograph 4 transmits the analysis status signal to the dissolution tester. Accordingly, in a case where the analysis is finished, the liquid chromatograph 4 transmits an analysis state signal indicating a state where a next sample can be analyzed, instead of a state where analysis is being performed.

In a case where there exists a sample for which the dissolution test is to be performed next (Step S37), whether the liquid chromatograph 4 is in an analyzable state is checked based on the analysis state signal transmitted from the analysis state communicating part 36 of the liquid chromatograph 4 (Step S32). If the liquid chromatograph 4 is an analyzable state for the next new sample, the next new sample is introduced into the test container and the dissolution test is started (Step S33). The liquid chromatograph 4 executes the analyzing operation on the next new sample in a similar manner as described above. As described above, in a case where a plurality of samples are installed in the dissolution tester 2, the operations of Steps S32 to S36 are automatically executed until the dissolution test of all the samples is completed.

DESCRIPTION OF REFERENCE SIGNS

2: Sample processing device
4: Liquid chromatograph
6: Arithmetic processing part
8: Liquid delivery device
10: Autosampler
12: Column oven
14: Detector
16: Inlet pipe
18: Outlet pipe
20, 22: Controller
24, 26: Communication interface
28: Mode selector
30: Immediate analyzing execution part
32: Collecting operation execution part
34: Collected sample analyzing execution part
36: Analysis state communicating part
38: Sampling needle
40: Injection port
42: Collection container
44: Flow vial
46: Flow vial rack
48: Flow vial main body
50: Cap
52: Septum
54: Inlet portion
56: Outlet portion

The invention claimed is:

1. A dissolution test system comprising a dissolution tester for performing a dissolution test of a sample and a liquid chromatograph, wherein
the liquid chromatograph includes:
an analysis channel through which a mobile phase flows;
an autosampler configured to inject a sample solution supplied from the dissolution tester into the analysis channel;
an analysis column separating individual components in the sample solution injected into the analysis channel by the autosampler;
a detector detecting the components separated by the analysis column; and
an analysis state communicating part configured to determine whether or not the liquid chromatograph is in an analyzing operation and to transmit an analysis state signal regarding whether or not the liquid chromatograph is in the analyzing operation to the dissolution tester, and
the dissolution tester includes a communicating part configured to receive the analysis state signal transmitted by the analysis state communicating part, in a case where a dissolution test is set to be executed continuously for a plurality of samples, the dissolution tester is configured not to start a dissolution test for a new sample when the liquid chromatograph is in the analyzing operation and to start a dissolution test for the new sample when the analyzing operation of the liquid chromatograph is finished, based on the analysis state signal received by the communicating part.

2. A liquid chromatograph used in the dissolution test system according to claim 1, further comprising:
a controller configured to control operation of at least the autosampler, wherein the liquid chromatograph is configured to perform the analyzing operation for the new sample when the dissolution tester starts a dissolution test for the new sample.

* * * * *